United States Patent [19]

Yun

[11] Patent Number: 5,125,113
[45] Date of Patent: Jun. 30, 1992

[54] VISORED CAP WITH FRONT, SIDE AND REAR SHADES

[76] Inventor: In-Seo Yun, E-block No. 5, Banpo Shopping Area, Banpobon-Dong, Seocho-ku, Seoul, Rep. of Korea

[21] Appl. No.: 693,348

[22] Filed: Apr. 30, 1991

[51] Int. Cl.$^5$ ............................................. A61F 9/00
[52] U.S. Cl. ............................. 2/10; 2/185 R; 2/195; 2/199
[58] Field of Search ............ 2/10, 12, 15, 171, 171.1, 2/175, 177, 181, 181.2, 181.4, 184.5, 185 R, 195, 196, 199, 209.1, 410, 425, 8

[56] References Cited

U.S. PATENT DOCUMENTS

| | | | |
|---|---|---|---|
| 1,232,812 | 7/1917 | Kirchner | 2/10 |
| 1,282,723 | 10/1918 | Altman | 2/10 |
| 2,266,967 | 12/1941 | Fuller | 2/10 |
| 2,363,461 | 11/1944 | Huntsman | 2/8 |
| 2,425,847 | 8/1947 | Vaca | 2/10 |
| 2,433,164 | 12/1947 | Shields | 2/8 |
| 2,475,471 | 7/1949 | Brown | 2/10 |
| 2,481,960 | 9/1949 | Wall | 2/10 |
| 2,500,280 | 3/1950 | Feldman | 2/10 |
| 2,523,885 | 9/1950 | Tannenbaum | 2/10 |
| 2,533,626 | 12/1950 | Reiter | 2/10 |
| 2,538,607 | 1/1951 | Vaca | 2/10 |
| 2,538,608 | 1/1951 | Vaca | 2/10 |
| 2,619,641 | 12/1952 | Vaca | 2/10 |
| 2,648,091 | 8/1953 | Jones | 2/10 |
| 2,654,089 | 10/1953 | Tannenbaum | 2/10 |
| 2,717,385 | 9/1955 | Linster | 2/10 |
| 2,897,510 | 8/1959 | Forbes-Robinson | 2/195 |
| 2,913,730 | 11/1959 | Schlesinger | 2/195 |
| 3,346,876 | 10/1967 | Hutton | 2/195 |
| 3,868,727 | 3/1975 | Paschall | 2/8 |
| 4,839,924 | 6/1989 | Laurence | 2/195 |
| 4,852,882 | 8/1989 | Otsuka | 2/199 |
| 5,007,110 | 4/1991 | Gilbert | 2/171 |
| 5,046,195 | 9/1991 | Koritan | 2/185 R |
| 5,056,164 | 10/1991 | Lisle | 2/185 R |

FOREIGN PATENT DOCUMENTS

| | | | |
|---|---|---|---|
| 494992 | 8/1953 | Canada | 2/175 |
| 52460 | 12/1936 | Denmark | 2/195 |
| 637556 | 5/1928 | France | 2/10 |
| 693217 | 11/1930 | France | 2/195 |
| 585529 | 3/1977 | Switzerland | 2/195 |
| 592424 | 10/1977 | Switzerland | 2/12 |
| 172583 | 12/1921 | United Kingdom | 2/195 |
| 1477818 | 6/1977 | United Kingdom | 2/199 |
| 2070413 | 9/1981 | United Kingdom | 2/209.1 |
| 90/03741 | 4/1990 | World Int. Prop. O. | 2/199 |

Primary Examiner—Werner H. Schroeder
Assistant Examiner—Diana L. Biefeld
Attorney, Agent, or Firm—Senniger, Powers, Leavitt & Roedel

[57] ABSTRACT

A visored cap includes a visor body having an elastic head rim and a cap body fixed detachably on the visor body. The visor body supports collapsibly a front shade and side shades. In addition, the front shade has at least a spare shade plate for controlling the intensity of the intercepted sunlight. The cap body supports collapsibly a rear shade.

7 Claims, 2 Drawing Sheets

VISORED CAP WITH FRONT, SIDE AND REAR SHADES

BACKGROUND OF THE INVENTION

1. Field of the Invention

This invention relates to a visored cap with front, side and rear shades, more particularly to a visored cap whose cap body is attachable to and detachable from a visor body supporting the front and side shades.

2. Description of the Related Art

Heretofore, such a visored cap for shading front and sides of a face have been known, in which mounted shade plates or cap cloths are extended downwards from both sides of the cap to form side shades. This known visored cap provides an effective sunshade, but can not allow its shape and construction to be varied according to the needs or tastes of users.

A visored cap, having a transparent eyeshade mounted collapsibly under the visor, is also known, providing adequately a vertical or horizontal eyeshade according to the situation. The fixed transparency of the eyeshade, however, can not accomodate itself appropriately to the change of intensity of sunlight.

For screening a face from the sun, in addition to the above mentioned kinds of visored caps, rimmed visors without cap bodies are also seen in the market. These existing visored caps and rimmed visors are not mutually interchangeable for the other purpose. That is, it is impossible to attach a cap body to a rimmed visor to use as a visored cap, or to detach a cap body from a visored cap to use as a rimmed visor.

SUMMARY OF THE INVENTION

Accordingly, an object of this invention is to provide a visored cap with front and side shades, which enables a cap body to be attached to and detached from a visor body, the front and side shades mounted on the visor body to be collapsed, and the front shade to have variable transparency, so that it can meet different situations and tastes of users.

Another object of this invention is to provide a visored cap which has a sweatband being detachable from a head rim in the visor body to provide easy washing of the soiled sweatband.

According to the invention, there is provided a visored cap comprising:

a visor body having integrally a partly cut-off annular head rim for gripping elastically a user's head;

a cap body, enclosing the head rim, wherein a lip is fixed detachably on the visor body by an attachment means;

a transparent front shade hingedly mounted under the front end region of the visor body by a hinge pin to take a horizontal position extended from the visor body or a vertical position to the visor body, and having at least a spare shade plate hingedly mounted on the hinge pin to overlap the front shade by a fixing means in the front shade or to be stored under the visor body in parallel with the visor body by a fixing means in the visor body; and two side shades collapsibly mounted on side edges of the visor body by hinge pins.

BRIEF DESCRIPTION OF THE DRAWINGS

Further objects and advantages of the invention can be more fully understood from the following description taken in conjunction with the accompanying drawings, in which.

DESCRIPTION OF THE PREFERRED EMBODIMENTS

Figure 1:
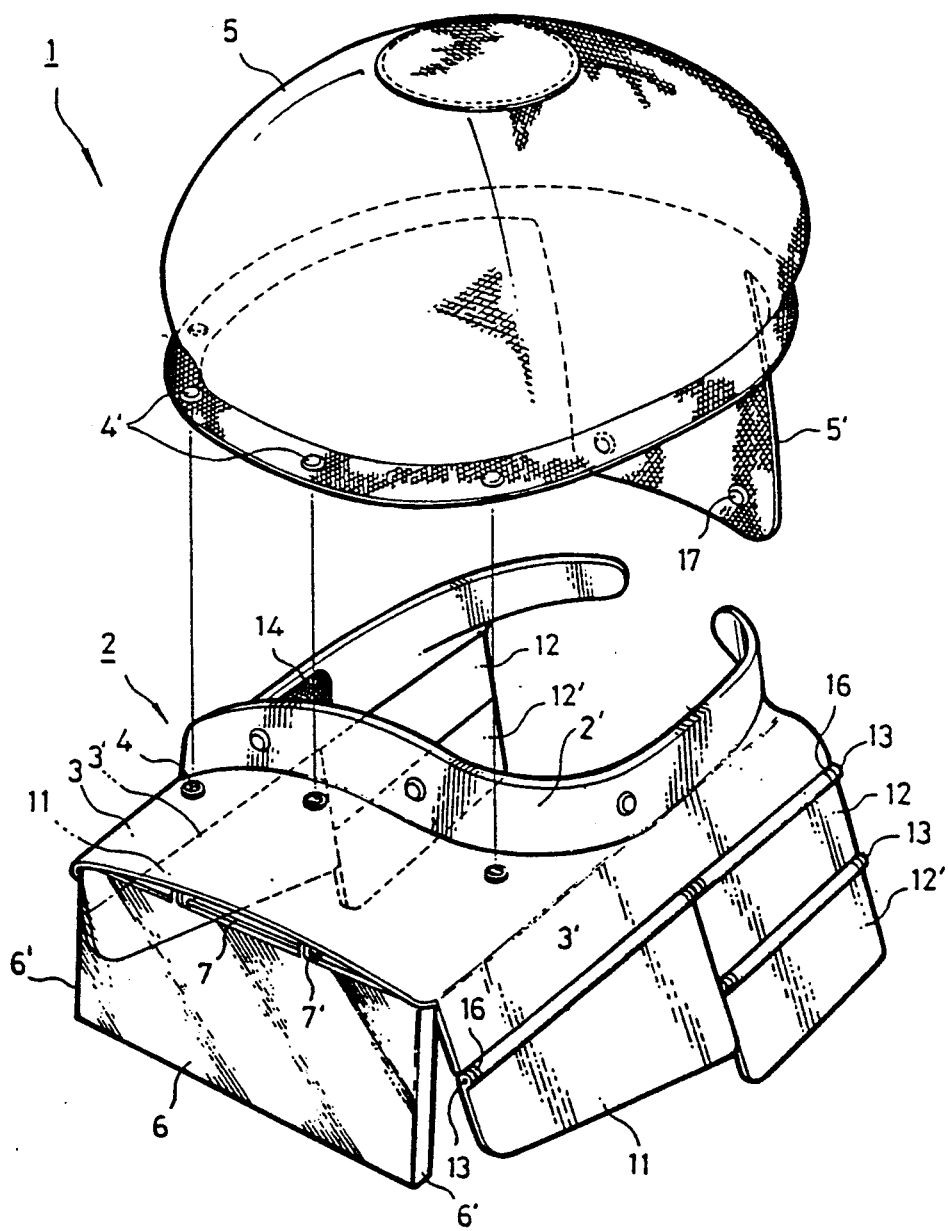
FIG. 1 is a perspective view showing a visored cap according to the invention, with a cap body detached from a visor body.

As shown in FIG. 1, a visored cap according to the invention has a visor 2 including a visor body 3 integrated with a partially cut-off annular head rim 2' and a cap body 5 fixed detachably on the visor 2 by an attachment means, which means is a plurality of snap fasteners 4 and 4' in this embodiment. The visored cap can be used as the cap body 5, attached or detached according to the tastes of users.

Figure 2:
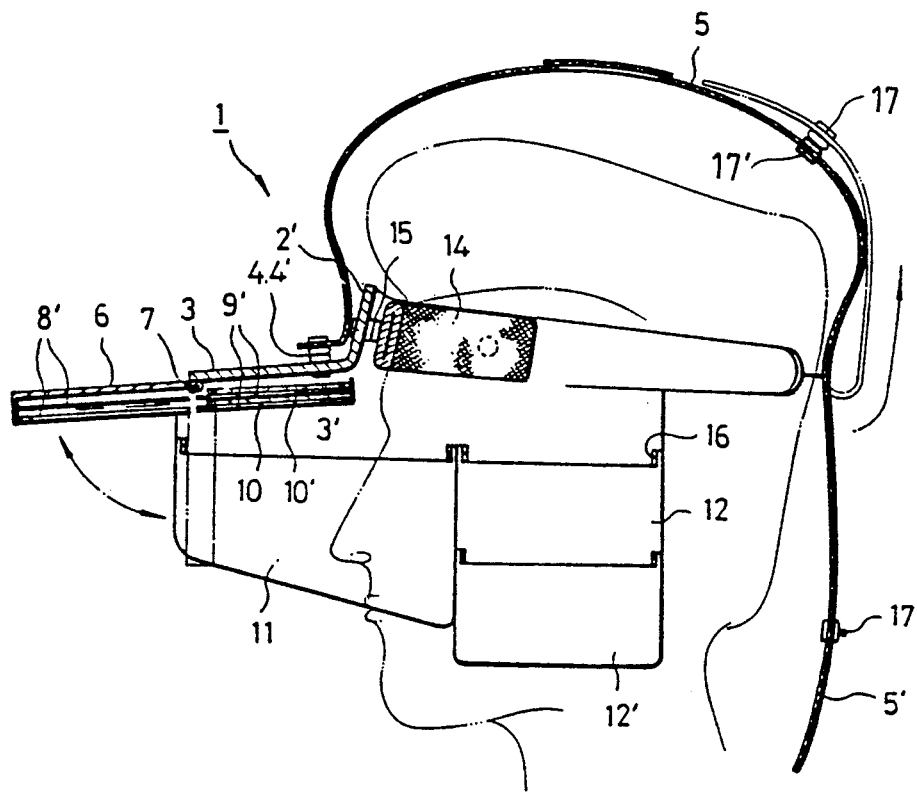
FIG. 2 is a sectional view of the visored cap with the cap body attached.
Figure 3:
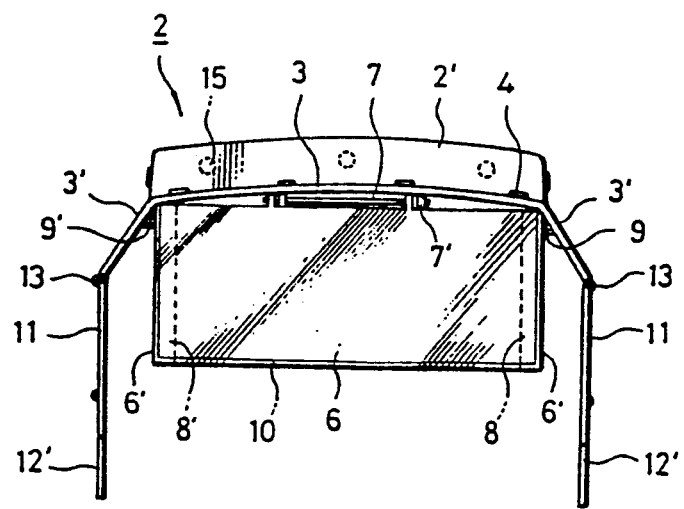
FIG. 3 is a front view of the visor body with shades.

Under the front end region of the visor body 3, a transparent front shade 6 is hingedly mounted by a hinge pin 7, and, as shown in FIG. 2, can be held in a horizontal position extended from the visor body 3 or a vertical position to the visor body 3 by a stopper 7', as shown in FIG. 3, formed on the visor body 3.

The front shade 6 has at least a spare shade plate 10 or 10' hingedly mounted on the common hinge pin 7. Normally, the spare shade plates 10 and 10' are held in a stored position under the visor body 3 in parallel therewith by stopper projections 9 formed thereon. As the situation demands, one or more spare shade plates 10 and 10' is or are pulled out from the stored position and overlapped on the front shade 6 to alter the transparency of the front shade 6. To this end, the front shade 6 has both side walls 6' formed with guide projections 8 and 8' toward the inside thereof to hold the spare shade plates 10 and 10'.

As shown in FIG. 3, on both side edges of the lateral bent extensions 3' of the visor body 3, side shades 11, 12 and 12' for shading sides of a face are hingedly mounted through hinge pins 13. These side shades can be collapsed upwards from the shown position. To hold the side shades in the collapsed position, the hinge pins 13 are provided with resilient washers 16.

Preferably, the side shades are divided into a front portion 11 and a rear portion, more preferably the rear portion is once again divided into an upper portion 12 and a lower portion 12'. The side shade portions 11, 12 and 12' are collapsibly mounted on the corresponding parts, thereby, the user can control the shading areas for the front side of his face or the rear side and this latter in an upper or lower direction.

The cap body 5 is preferably provided with a rear shade 5' for shading the back of the neck from the sun. The rear shade 5' is formed as an extension of the cap body 5 and is normally folded up on the cap body 5 through snap fastener 17, 17'. In case of need, the rear shade 5' is freed from the snap fastener 17, to lower to effect shading.

In addition, in an advantageous embodiment of this invention, the head rim 2' for elastically gripping a user's head has a sweatband 14 fixed detachably thereon by appropriate attachment means such as for example snap fasteners 15 in FIG. 2. Thereby the soiled sweatband 14 can be easily detached from the head rim 2' to be washed.

As described above, the visored cap according to this invention provides effective shading for the front and side face and the back of the neck through various modifications in accordance with the intensity of the sunlight or the tastes of users.

Modifications and variations of the present invention are possible in light of the above teachings. It is therefore to be understood that within the scope of the appended claims, the invention may be practiced otherwise than as specifically described.

What is claimed is:

1. A visored cap comprising:
   a visor body having integrally a partly cut-off annular head rim for gripping elastically a user's head;
   a cap body, enclosing said head rim, wherein a lip is fixed detachably on said visor body by an attachment means;
   a transparent front shade hingedly mounted under a front end region of said visor body by a hinge pin to take a horizontal position extended from said visor body or a vertical position to said visor body, and having at least a spare shade plate of a different light transparency hingedly mounted on said hinge pin to be overlapped on said front shade by a first fixing means formed in said front shade or to be stored under said visor body in parallel therewith by a second fixing means formed in said visor body; and
   side shades collapsibly mounted on both side edges of said visor body by hinge pins.

2. A visored cap according to claim 1, wherein said side shades are divided into a front and a rear portion respectively.

3. A visored cap according to claim 2, wherein said rear portions of said side shades are divided into an upper and a lower portion respectively.

4. A visored cap according to claim 1, wherein said attachment means of said cap body is a plurality of snap fasteners.

5. A visored cap according to claim 1, said head rim thereof including a sweatband being attachable thereon and detachable therefrom.

6. A visored cap according to claim 1, said cap body thereof including a rear shade which is extended from said cap body and can be folded up thereon or down therefrom by an attachment means.

7. A visored cap according to claim 1, wherein said spare shade plates are multiple in number and of different sunlight transmissivities.

* * * * *